(12) United States Patent
Jensen et al.

(10) Patent No.: US 6,855,129 B2
(45) Date of Patent: Feb. 15, 2005

(54) SAFETY NEEDLE ASSEMBLY

(75) Inventors: Karsten Jensen, Hjorring (DK); Niels Nymark, Hjorring (DK)

(73) Assignee: Novo Nordisk A/S, Bagsvaerd (DK)

( * ) Notice: Subject to any disclaimer, the term of this patent is extended or adjusted under 35 U.S.C. 154(b) by 135 days.

(21) Appl. No.: 10/307,054

(22) Filed: Nov. 29, 2002

(65) Prior Publication Data
US 2003/0120209 A1 Jun. 26, 2003

Related U.S. Application Data
(60) Provisional application No. 60/343,045, filed on Dec. 22, 2001.

(30) Foreign Application Priority Data
Nov. 30, 2001 (DK) ................................. PA 2001 01772

(51) Int. Cl.[7] .......................... A61M 5/00; A61M 5/32
(52) U.S. Cl. ..................... 604/110; 604/198; 604/263
(58) Field of Search .............................. 604/110, 263, 604/164.08, 192, 198; 128/919

(56) References Cited

U.S. PATENT DOCUMENTS

| | | | |
|---|---|---|---|
| 4,894,055 A | 1/1990 | Sudnak | 604/198 |
| 5,346,480 A | 9/1994 | Hess et al. | 604/197 |
| 5,433,712 A | 7/1995 | Stiles et al. | 604/197 |
| 5,688,241 A | * 11/1997 | Asbaghi | 604/110 |

FOREIGN PATENT DOCUMENTS

| | | |
|---|---|---|
| WO | 95/29721 | 11/1995 |
| WO | 99/32177 | 7/1999 |
| WO | 01/76665 A1 | 10/2001 |

* cited by examiner

*Primary Examiner*—Brian L. Casler
*Assistant Examiner*—Catherine S. William
(74) *Attorney, Agent, or Firm*—Marc A. Began, Esq.; Reza Green, Esq.; Richard W. Bork, Esq.

(57) ABSTRACT

The invention relates to a safety needle assembly for injecting a fluid into a human body comprising a cylindrical housing with a bottom surface supporting a needle cannula and a shield telescopically movable relative to the housing. A spring located within the housing urges the shield in a distal needle covering direction and a locking member also provided inside the housing moves simultaneously with the shield during injection and automatically locks the shield in a position where the sharp end of the needle cannula is concealed thereby irreversible immobilizing the safety needle assembly.

9 Claims, 14 Drawing Sheets

SAFETY NEEDLE ASSEMBLY

CROSS REFERENCE TO RELATED APPLICATIONS

This application claims the benefit of priority of U.S. provisional application No. 60/343,045, filed Dec. 22, 2001 and Danish Application PA 2001 01772, filed Nov. 30, 2001; the contents of both are hereby incorporated by reference in their entirety.

FIELD OF THE INVENTION

The invention relates to a safety needle assembly, which reduces the risk of accidental needle-stick injuries, and especially a safety needle assembly where a needle cannula is mounted in a hub.

Description of Related Art

Needle assemblies are commonly used to either inject substances into or extract substances out of human or animal bodies. Such needle assemblies are typically disposable and are discarded after only one use. The problem presented by the disposal of a needle assembly, and indeed, by any handling of the needle assembly, is the potential risk of being injured by the sharp end of the needle cannula. This is particular dangerous when following after the penetration of a patients skin since the needle cannula then may be contaminated and therefore capable of spreading diseases such as hepatitis and HIV.

A great number of safety needle assemblies has been developed where the needle cannula is concealed by a telescopically movable shield during the injection.

One such prior art needle protection system is disclosed in WO 01.76665. This safety needle comprises a hub with a centrally located needle cannula. A telescopically movable shield is provided on the outside surface of the hub. The shield is telescopically movable between a first position where it fully covers the needle cannula and a second position where a part or the needle cannula is left free to perform an injection. A cam element, rotatable mounted to the hub is provided with at least one cam, which cam is guided in cam curve provided in the inside surface of the shield. The shield is urged in the distal direction by a spring cocked between the hub and the shield. The cam curve is adapted to block the cam in a blocking position when the shield returns to the first position after an injection has been performed.

The safety needle assembly disclosed in WO 01.76665 is however rather cumbersome and consist of a large number of parts that must be moulded and afterwards fitted together very precisely in order to obtain the correct movement of the cam follower.

It is also a fact that the different plastic parts of an assembled construction have a tendency to change the relative dimensions when the construction is sterilized using steam or gas. This is especially critical when the tolerances have to be very narrow, as in the safety needle assembly disclosed in WO 01.76665.

In order to assure that the cam element of WO 01.76665 in fact shifts into the locked position when the protective cap moves back to the initiate position after an injection has been made, a rather powerful spring is needed. This is an inconvenience for the user, since the user has to press the protective cap in the proximal direction literally with the use of his or hers skin while making the injection.

DESCRIPTION OF THE INVENTION

It is henceforth an object of the present invention to provide a safety needle assembly, which overcomes the inconveniences of the prior art safety needle assemblies, and especial to provide a safety needle assembly which is made from fewer parts, and which parts are not subject to very strict tolerances.

It is further an objective of the present invention to provide a safety needle assembly having a spring with only a limited force thereby offering the user maximum comfort.

In order to overcome the drawbacks of the prior art it is suggested to provide the safety needle assembly with a separate locking element located between the spring and the shield according to claim 1.

When the locking element is provided as a separate element located between the spring and the shield and moved simultaneously with the shield, the locking protrusion can be guided during the longitudinal movement of the locking member thereby eliminating the need for tracks or cams thus making it possible to construct the safety needle assembly from only three plastic part in addition to the hub.

Since there are no tracks or cams as such the internal tolerances are not that important, and the friction can be kept rather low which renders it possible to utilize a somewhat soft spring, which enhances the user comfort.

By blocking the rotational movement of the locking protrusion with a fin provided on the inside surface of the housing as specified in claim 2, it is possible to define when the rotatable movement of the locking protrusion should commence simply by specifying a specific length of the fin.

Once the locking protrusion on the locking element has passed over the end of the fin as specified in claim 3 it will be impossible to move the locking protrusion backwards. The length of the fins can be made such that once the shield has been activated and the needle cannula has emerged from the opening in the shield it will be impossible to abort the injection and keep the needle for later use.

When the locking protrusion engages the toothed ring of the shield as defined in claim 4, the shield can be moved all the way back in the proximal direction thereby uncovering the needle cannula.

When the injection is over and the locking protrusion is arrested in the opening in the longitudinal rib as mentioned in claim 5, it is virtually impossible to advance the needle cannula again by pressing the shield backwards in the proximal direction.

The guiding means for guiding the locking protrusion comprises only horizontally difined ribs and fins as specified in claim 6. This makes both the moulding of the parts and the assembly of the parts very simple.

By mounting the shield inside the housing as disclosed in claim 7, it is ensured that the shield cannot be separated from the housing.

When the spring cocked between the locking element and the hub interfaces both the locking element and the bottom surface of the housing as revealed in claim 8, it is ensured that the spring can be added to the assembly in a very simple manner.

By providing the housing with a window through which the locking protrusion can be viewed when it is in the arrested position, it is ensured that a user can visible inspect whether the safety needle assembly has been used before or not.

The part of the shield and/or the locking element that are visible through the window when the safety needle assembly is in the unused condition can also be coloured in a colour indicating that the safety needle assembly is ready for use.

The window can either be transparent or simply an opening in the sidewall of the housing.

In the present context, the term "moving simultaneous" which are used to describe the relationship between the movement of the shield and the locking element, does not necessary mean that the shield and the locking protrusion moves with the same speed. The relative speed of movement is defined by the various angled surfaces, and is therefore variable. The term "moving simultaneously" merely means that both the shield and the locking protrusion move at the same time.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

Initially it may be convenient to define that, the term "distal end" is meant to refer to the end of the safety needle assembly inserted into the patient, whereas the term "proximal end" is meant to refer to the end connected to the injection device.

Figure 1:
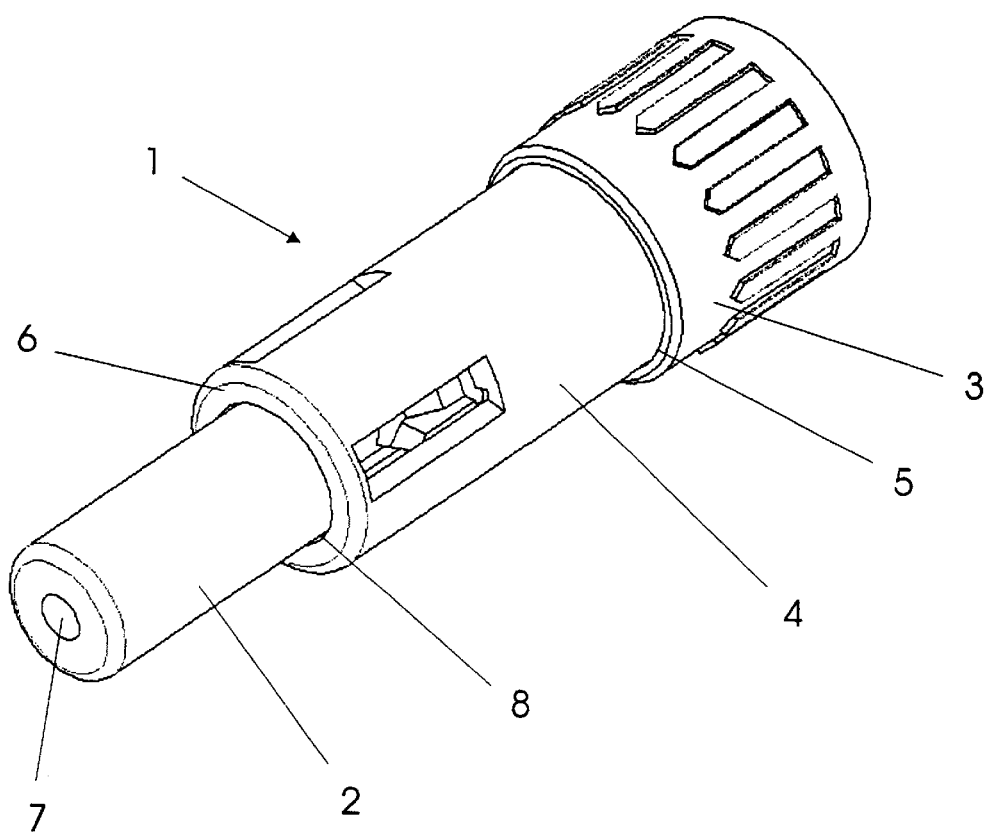
FIG. 1 Shows a perspective view of the safety needle assembly according to the invention.

FIG. 1 shows a safety needle assembly comprising a housing 1 and a shield 2, the housing 1 is made up from a hub 3 and a body 4. The hub 3 and the body 4 is normally glued or welded together.

The connecting surface 5 between the hub 3 and the body 4 is in the figures shown in a specific position, but could off cause be located as wanted. The hub 3 and the body 4 could even be moulded as one piece closed at the top surface 6 by a lit. The top surface 6 is provided with an opening 8 through which the shield 2 appears.

The shield 2 is provided with a needle outlet 7 through which the needle cannula 30 can penetrate. The proximal end of the shield 2 is, as shown in FIG. 2, provided with eight outwardly projecting studs 10, which studs 10 has a planar fore front 11 and an angled back front 12.

The housing 1 has a bottom surface 9 in the centre of which the needle cannula 30 is mounted. The needle cannula 30 can either be mounted such that a part of needle cannula 30 projects from the bottom surface 9 in the proximal direction, which is preferred for use with cartridges, or it can be mounted without this so called back needle, which is preferred for hypodermic syringes. Adjacent the bottom surface 9, at the proximal end of the housing 1, means are provided for mounting the safety needle assembly on to an injection device. These means would normally be a thread 35 such that the safety needle assembly can be screwed onto a pen syringe.

Figure 3:
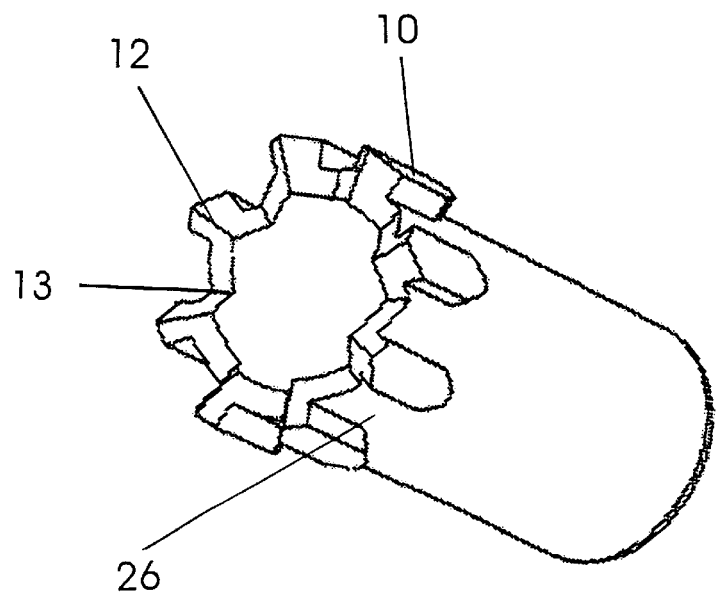
FIG. 3 Shows a perspective view of the needle shield.

FIG. 3 shows the shield 2 seen from the proximal end. The eight studs 10 are separated from each other by eight equally sized spaces 26. The angular back front 12 of the studs 10 forms together with the shield 2 a toothed ring 13 where the centre of the studs 10 forms the tops and the shield 10 within the spaces 26 forms the valleys.

Figure 2:
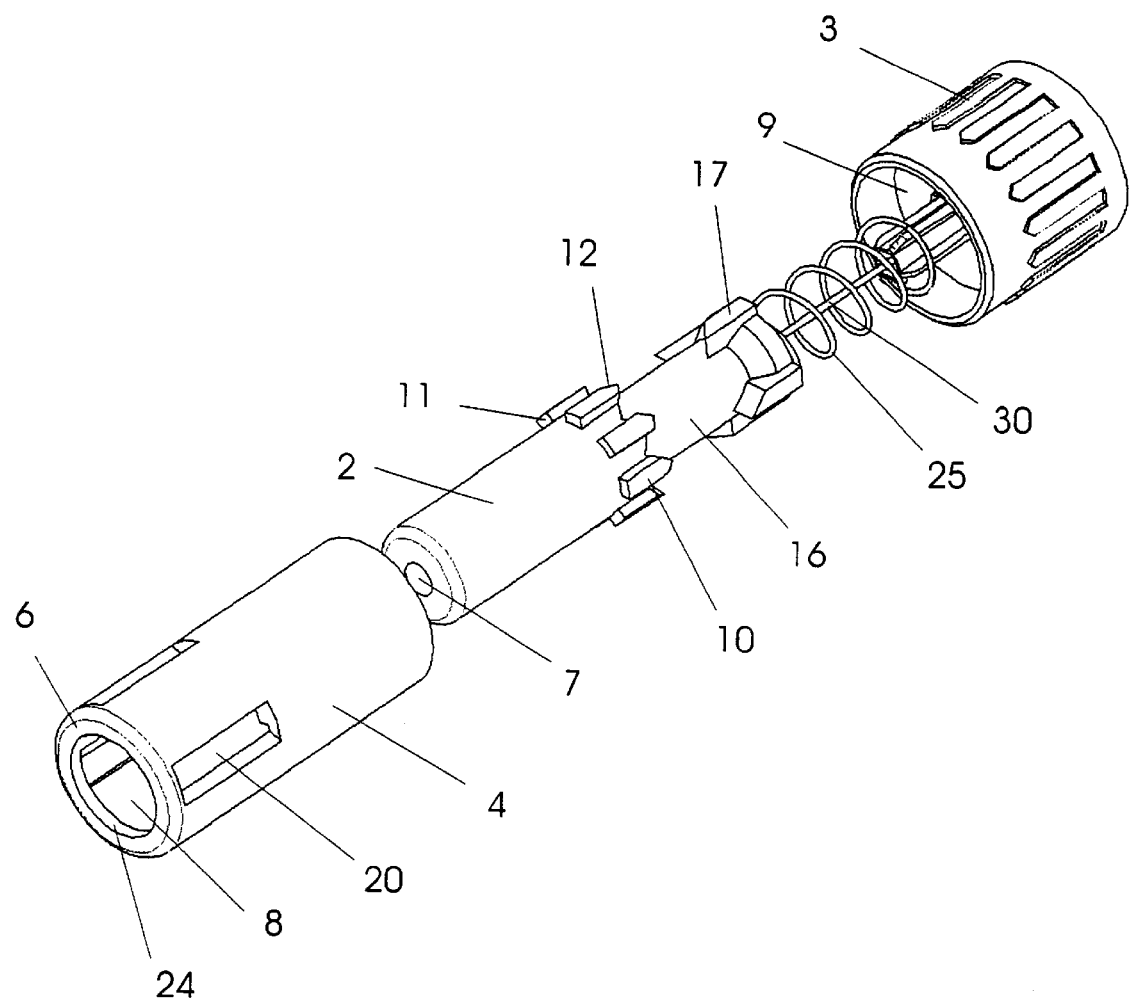
FIG. 2 Shows an exploded view of the safety needle assembly according to the invention.
Figure 4:
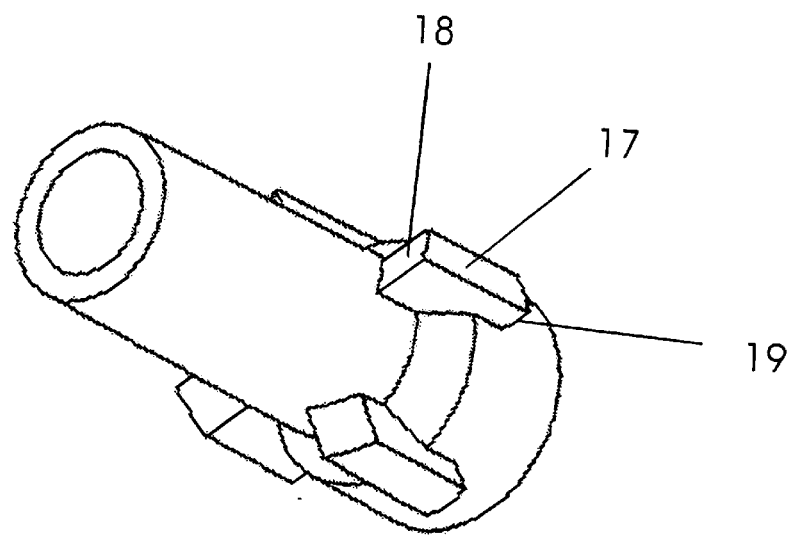
FIG. 4 Shows a perspective view of the locking element.

The locking element 16 seen in FIG. 2 is on the proximal outside surface provided with four locking protrusions 17. These locking protrusions 17 have, as shown in FIG. 4, an angled fore front 18 and a planar back front 19.

Figure 5:
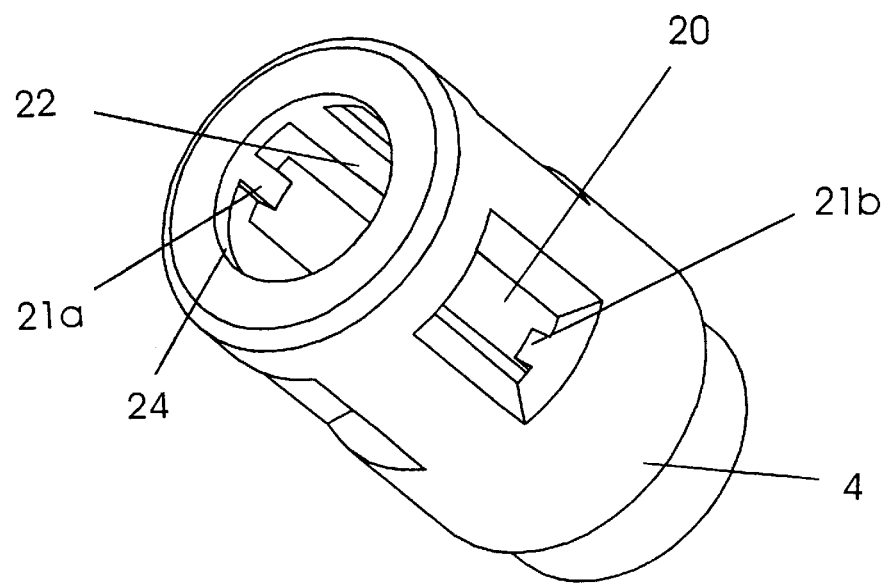
FIG. 5 Shows a perspective view of the body of the housing.
Figure 6:
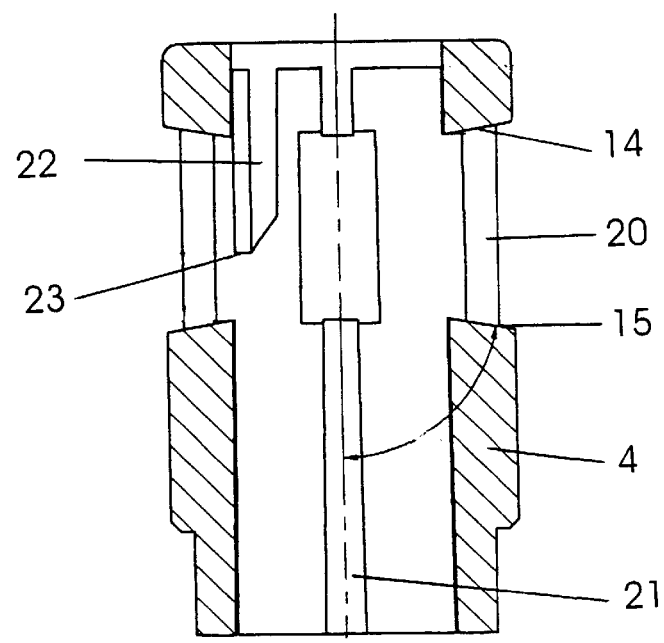
FIG. 6 Shows a schematically view of the body of the housing.

The body 4 of the housing 1 is in FIG. 5 shown in perspective and in FIG. 6 in a sectional view. The body 4 is provided with four windows 20 and one longitudinal rib 21 for each window 20. The ribs 21 are provided on the inside surface of the body 4. These longitudinal ribs 21 extend through the entire length of the body 4 although divided into two parts (21a, 21b) by the windows 20. The distal part of this rib 21 is moulded uniform with a collar 24 provided at the distal end of the body 4 and terminates in a planar surface 14 at the distal end of the window 20. The proximal part of the rib 21 terminates at the proximal end of the window in a blocking surface 15, the use of which will be explained later. At the distal end of the body 4 there is provided four fins 22. These fins 22 is moulded uniform with the collar 24 at the distal end of the body 4, and has at the proximal end an angled surface 23 which terminates approximately in a position adjacent the middle of the windows 20.

Figure 15:
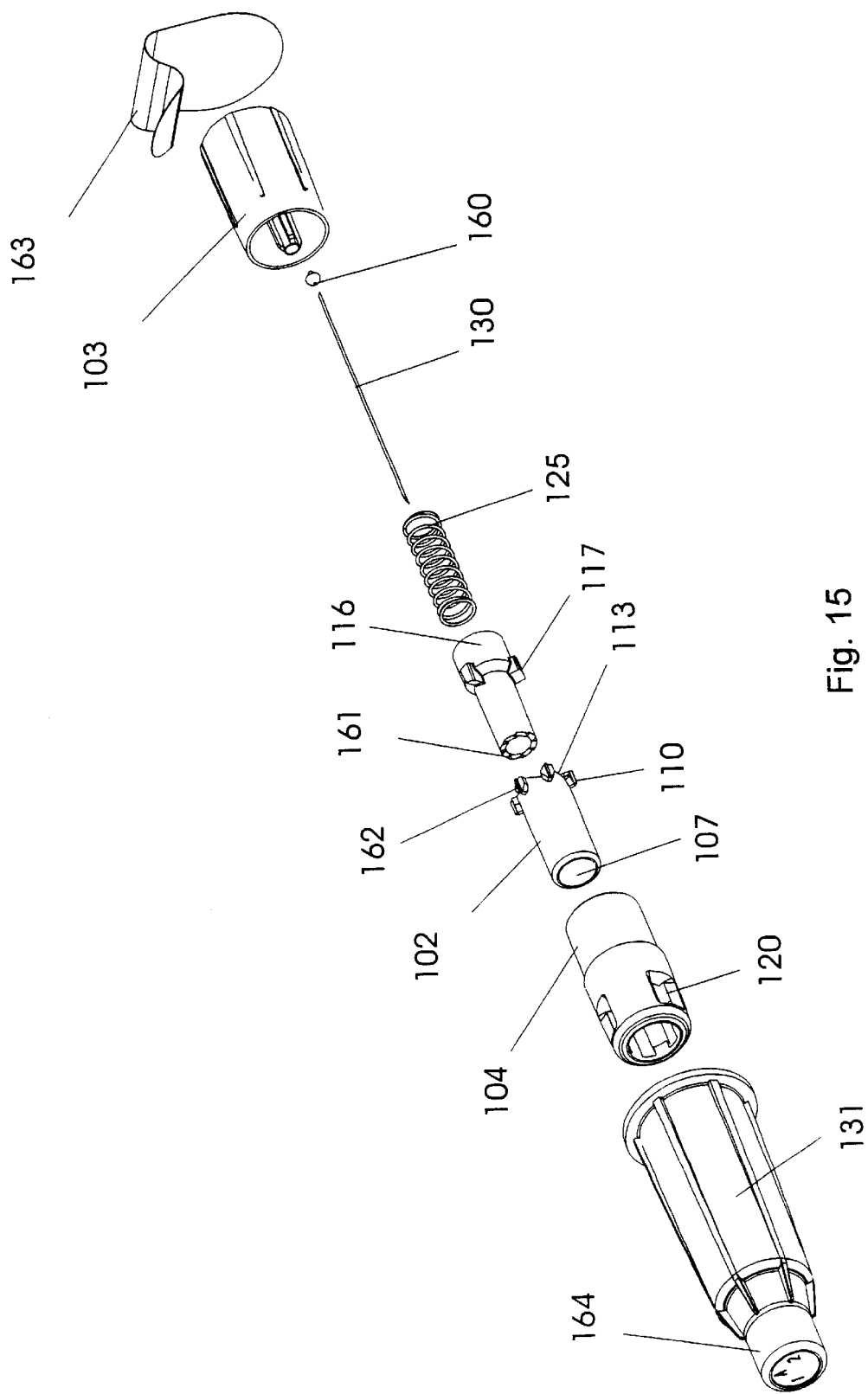
FIG. 15 Shows an exploded view of the safety needle assembly according to the invention.

Although the embodiment here described has eight studs 10, four locking protrusions 17 and four windows 20, these parts could be provided in a different number, as shown in FIG. 15.

When the safety needle assembly shown in FIG. 2 is assembled, a spring 25 is cocked between the bottom surface 9 of the housing 1 and the locking element 16 urging the locking element 16 and the shield 2 in a distal direction. The planar forefront 11 on the studs 10 abuts the collar 24 such that the shield 2 is connected to the body 4 of the housing 1.

Figure 7:
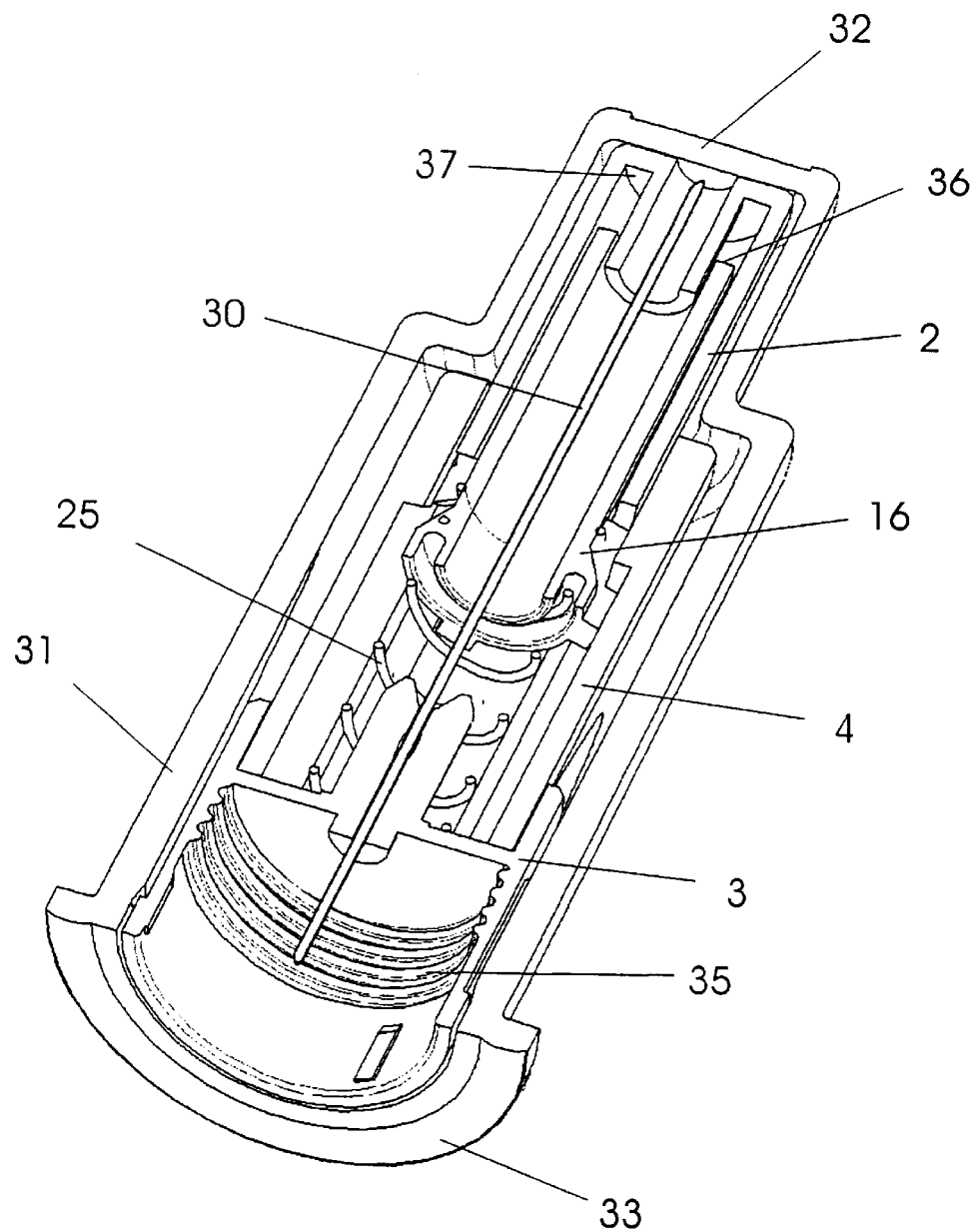
FIG. 7 Shows a schematically view of the safety needle assembly according to the invention.
Figure 8:
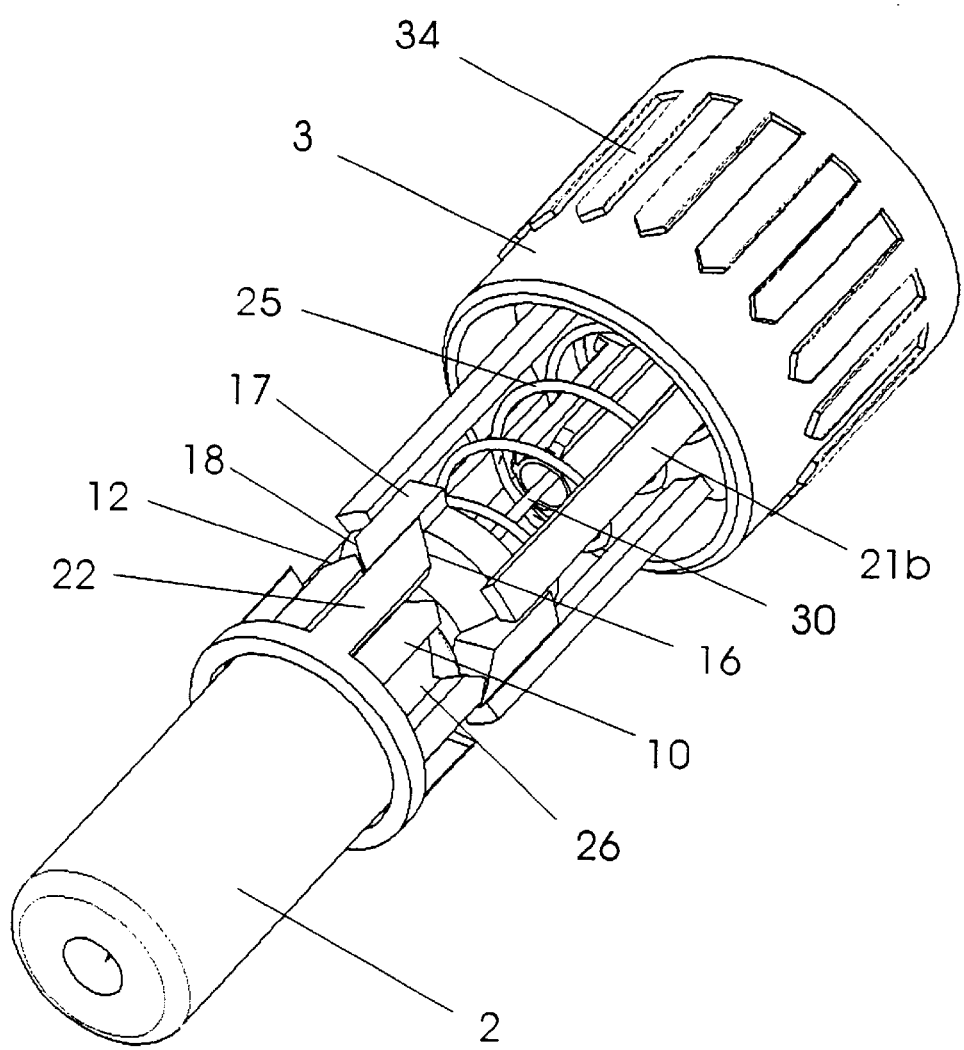
FIG. 8 Shows a schematically view of the safety needle assembly according to the invention, with a part of the housing cut away.

The assembled safety needle assembly is shown in FIGS. 7 and 8. FIG. 8 illustrates the inside of the safety needle assembly with the body 4 cut away.

The shield 2 is located such within the body 4 of the housing 1 that each rib 21 and each fin 22 is located in the space 26 between two studs 10. The upper part 21a of the ribs 21 are however not shown in FIG. 8, since this upper rib 21a is not entirely necessary. The locking element 16 is thereafter mounted such that the angular forefront 18 on each locking protrusion 17 abuts the angled back front 12 on four of the studs 10 of the shield 2, whereby the side surface of the locking protrusion 17 and the side surface of the studs 10 forms a straight line which line abuts the side surface of the fins 22 of the body 4 of the housing 1.

Once the shield 2 and the locking element 16 is correctly mounted within the body 4 of the housing 1, the spring 25 is located around the needle cannula 30 and the body 4 and the hub 3 are sealed together, rendering the safety needle assembly ready for use.

The movement of the locking protrusion 17 is schematically shown in FIGS. 9–12, showing the relative position of one of the locking protrusion 17 on the locking element 16, two of the studs 10 on the shield 2, one of the fins 22 on the inside surface of the body 4 of the housing 1 and one of the ribs 21 also located on the inside surface of the body 4 of the housing 1.

Figure 9:
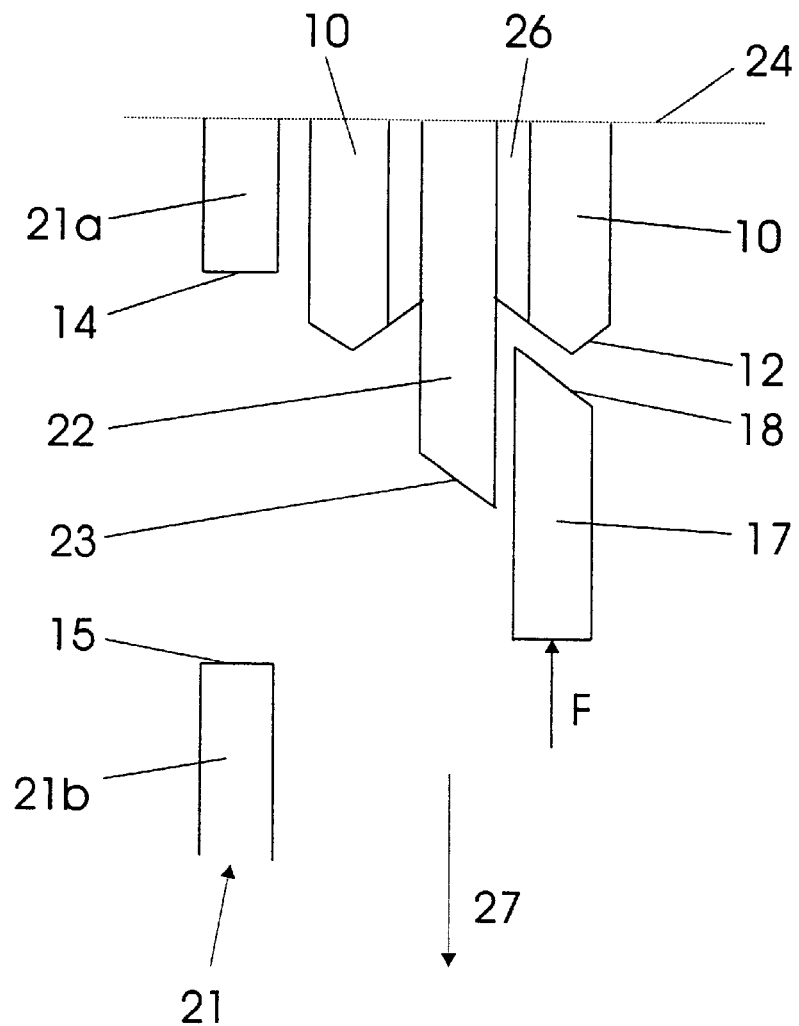
FIG. 9 Shows the locking protrusion in its first position.

FIG. 9 illustrates the safety needle assembly in its initial position, as shown in FIG. 8, with the shield 2 in its distal position where the shield 2 covers the needle cannula 30. When the shield 2 is pressed towards the skin of a user, the shield 2 and with it the studs 10, are moved in a proximal direction as indicated with the arrow 27. This movement also moves the locking protrusion 17 on the locking element 16 in the proximal direction against the force F of the spring 25.

Figure 10:
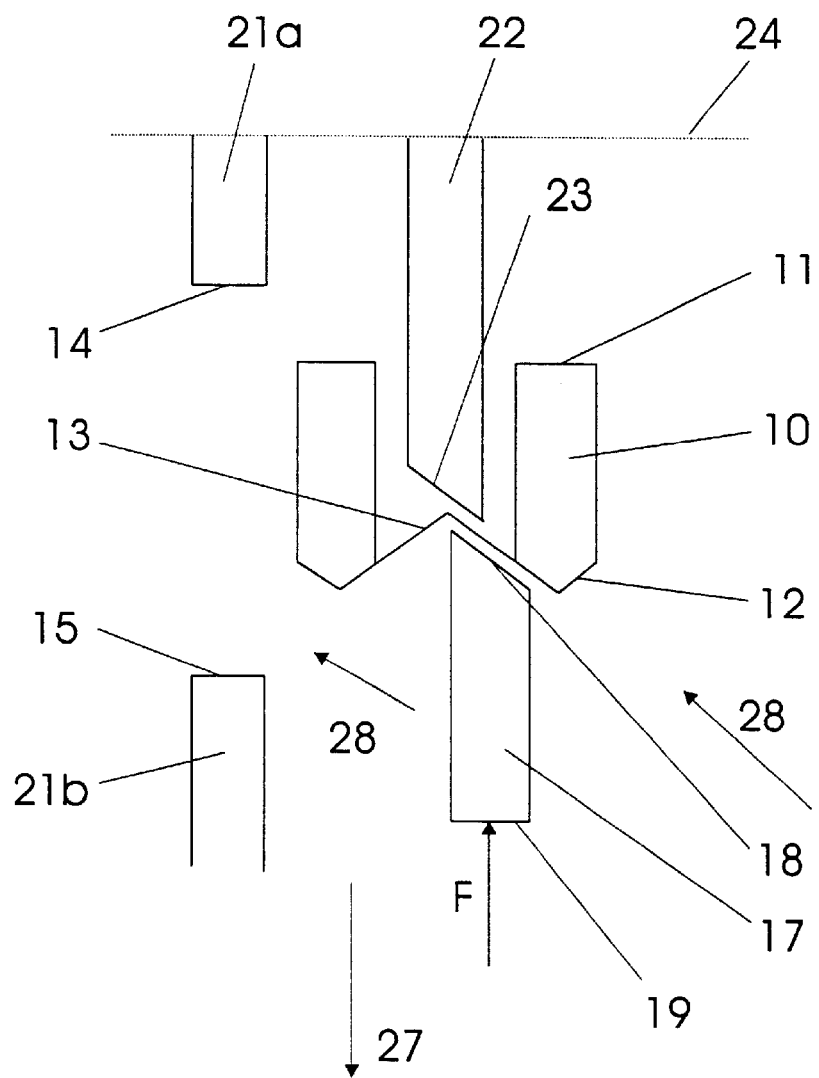
FIG. 10 Shows the locking protrusion in or moving towards its second position.
Figure 11:
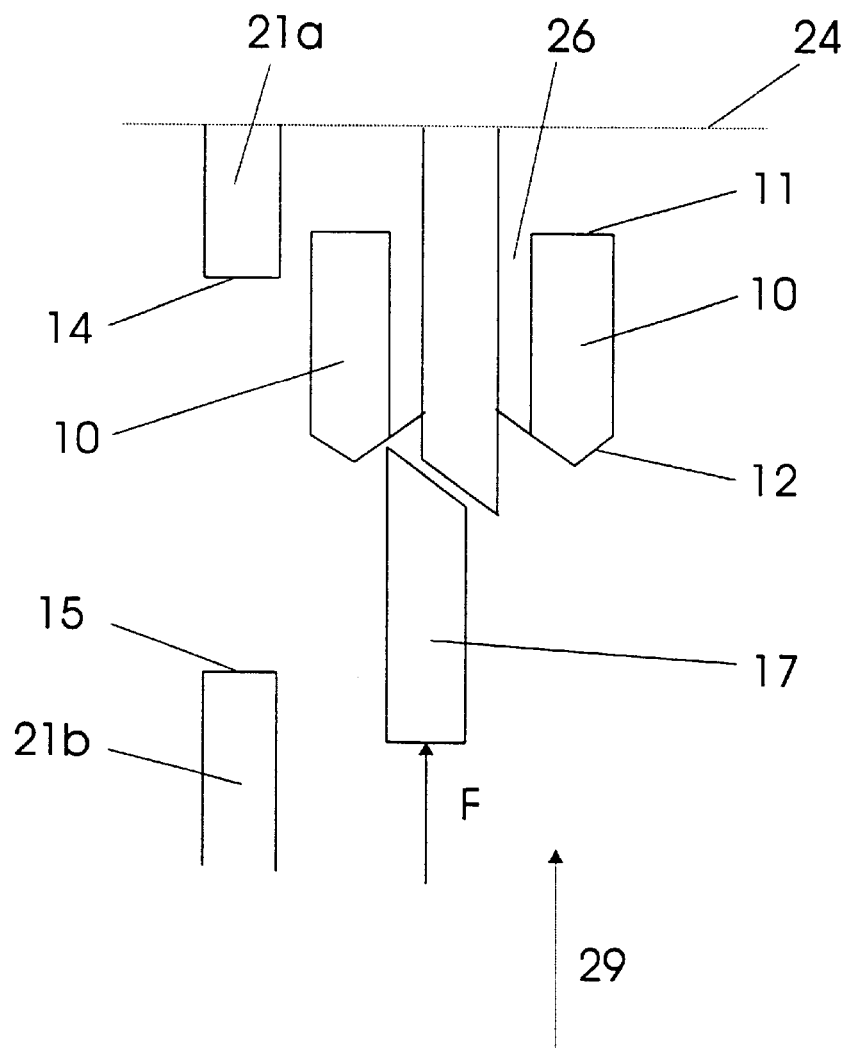
FIG. 11 Shows the movement of the locking protrusion moving from the second to the third position.

Once the locking protrusions 17 is moved free of the fins 22, as shown in FIG. 10, the angled fore front 18 of the locking protrusions 17 will slide along the angled back front 12 of the studs 10 and the angled fore front 23 of the fins 22 as indicated with the arrow 28. This movement will move the locking protrusions 17 into contact with the valleys of the toothed ring 13. Further movement of the shield 2 and thereby the studs 10 in the direction of the arrow 27 will only move the locking protrusions 17 further in the proximal direction. The injection is then executed with the shield 2 in its most proximal direction. The position of the fins 22 and the ribs 21 is such that the studs 10 are always guided either by the fins 22 or by the ribs 21.

When the injection is over, the needle cannula 30 is retracted from the skin of the user, which will cause the shield 2 with the studs 10 and the locking element 16 with the locking protrusion 17 to move in the distal direction due to the impact of the force F executed by the spring 25. The arrow 29 in FIG. 11 indicates this movement.

Figure 12:
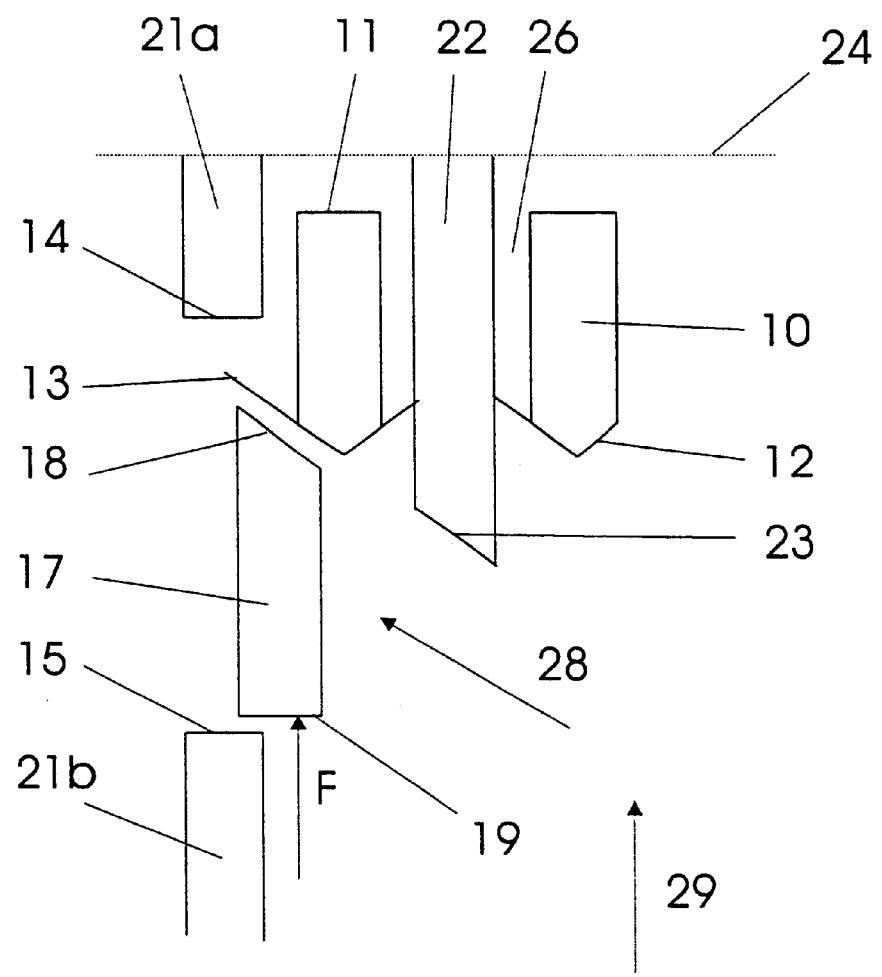
FIG. 12 Shows the locking protrusion in the third position.

FIG. 12 illustrates how the force F of the spring 25 urges the locking element 16 with the locking protrusion 17 and the shield 2 with the studs 10 in the distal direction. When the angled fore front 23 on the fins 22 aligns the angled back front 12 of the studs 10, such that the two angled fore fronts 23, 12 form a diagonal line, the angled fore front 18 of the locking protrusion 17 will slide along this line into a position where the locking protrusion 17 is located between the upper part 21a and the lower part 21b of the ribs 21 i.e. between the planar surface 14 of the upper part 21a of the ribs 21 and the blocking surface 15 of the lower part 21b of the ribs 21. In this position the locking protrusion 17 and hence the locking element 16 and the shield 2 is irreversible locked.

At the proximal end of the locking protrusion 17, the planar back front 19 will abut or at least be blocked by the blocking surface 15 on the ribs 21 of the body 4 of the housing 1, thereby rendering it impossible to move the shield 2 in the proximal direction. At the distal end, the angled fore front 18 of the locking protrusion 17 will abut the toothed ring 13 of the shield 2 and since the planar forefront 11 of the studs 10 on the shield 2 abuts the collar 24 of the body 4 of the housing 1 it will not be possible to move the shield 2 in the distal direction. Sideways the studs 10 of the shield 2 will be arrested between the upper part 21a of the ribs 21 and the fins 22. As a result of this it will be impossible to move the shield 2 in any direction.

Instead of having the angled fore front 18 of the locking protrusion 17 in abutment with the toothed ring 13 of the shield when the injection is over, the front end 36 of the locking element 16 can be design to abut the inner top end 37 of shield 2 once the locking protrusion 17 is in the locking position. This will make it virtually impossible to squeeze the angled fore front 18 of the locking protrusion 17 by pushing the shield 2 in the proximal direction.

The body 4 of the housing 1 is provided with four windows 20 which windows 20 divides each of the four ribs 21 into an upper part 21a and a lower part 21b. When the safety needle assembly has been used, the locking protrusion 17 on the locking element 16 will be located between the upper part 21a and the lower part 21b of the ribs 21, and will thus be visible through the window 20. The locking protrusion 17, or a part of it, could be coloured in an inflammatory colour, or provided with another indication, which will render it very easy for a user to visibly inspect whether the safety needle assembly has been used or not just by glancing at the windows 20. The windows 20 could e.g. be provided as openings in the wall of the body 4.

Prior to use, the safety needle assembly is delivered to the user sterilized and contained as is shown in FIG. 7. The container 31 is closed at the distal surface 32 and open at the proximal surface 33. The proximal surface 33 is sealed by a not shown removable seal. The container 31 has on the inside surface not shown ribs that mates ribs 34 located on the outside surface of the housing 1 preferably on the hub 3, such that the safety needle assembly can be screwed on and off a pen syringe without removing the container 32 from the safety needle assembly. Further the container could on the inside surface be provided with a number of not shown raised points supporting the safety needle assembly in a somewhat floating position making it easier for the steam or gas to fully surround the safety needle assembly during sterilization in case this type of sterilization is used.

The spring 30 urging the locking element 16 and the shield 2 in the distal direction is preferably made from stainless non-corrosive steel such that the spring 30 will not be damaged during the steam sterilization process. A spring 30 particular suitable for this purpose is a 1.4462/SAF2205 spring.

Figure 13:
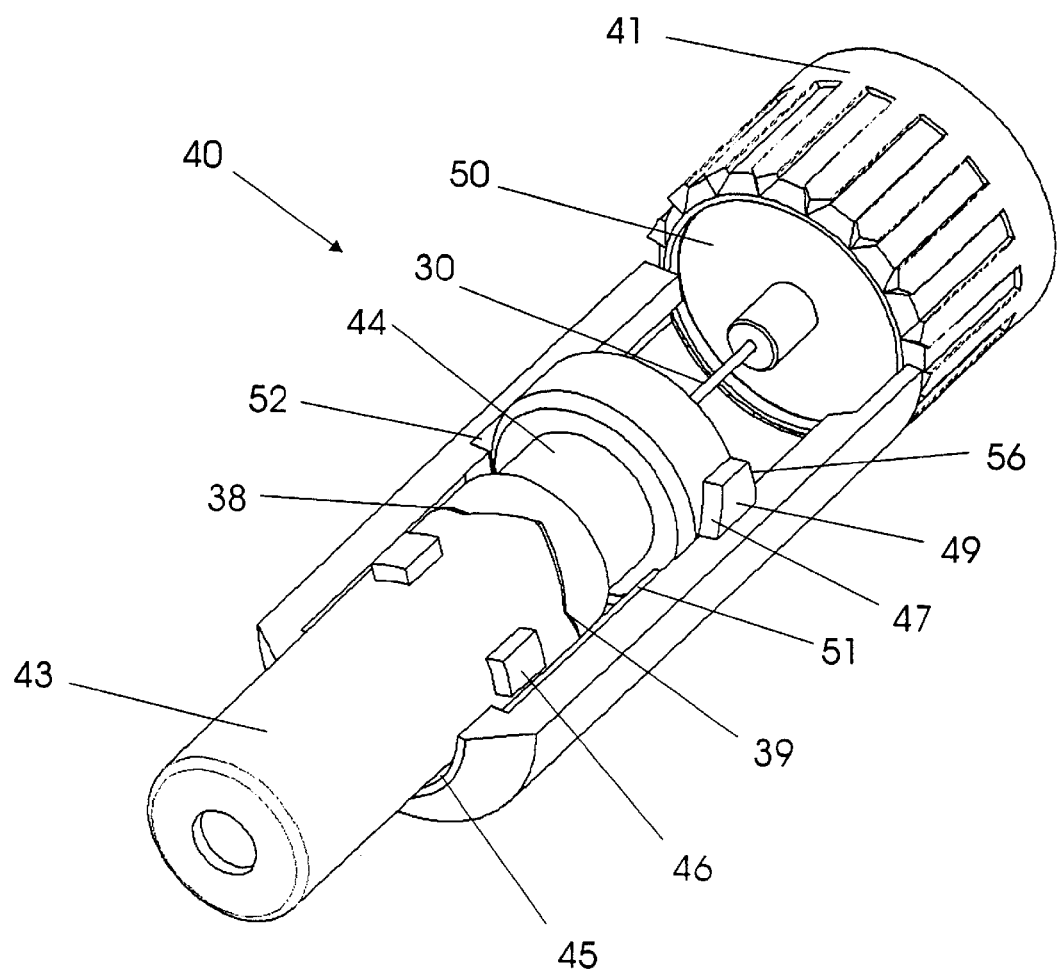
FIG. 13 Shows a perspective view of an embodiment of the safety needle assembly according to the invention.
Figure 14:
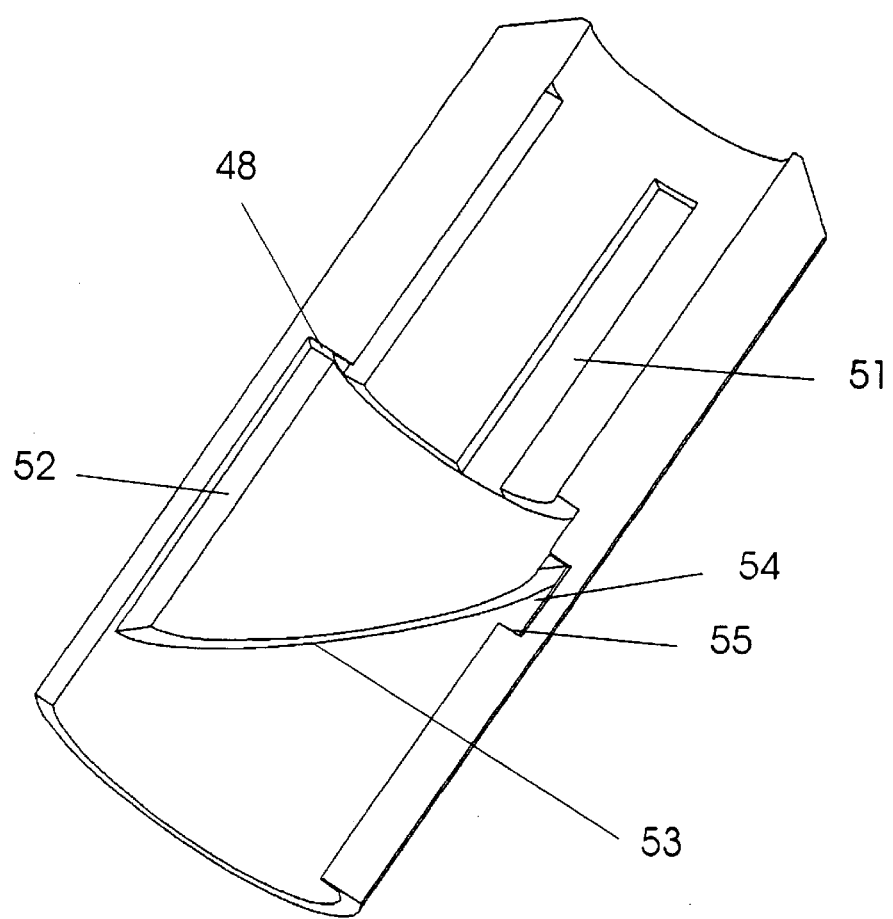
FIG. 14 Shows a part of the housing of an embodiment of the safety needle assembly according to the invention.

Another embodiment of the safety needle assembly according to the invention is disclosed in FIG. 13 and FIG. 14.

FIG. 13 shows a housing 40 comprising of a hub 41 and body 42. Mounted inside the housing 40 are a shield 43 and a locking element 44. The shield 43 penetrates out of the housing 40 through an opening 45 located at the distal end of the housing 40

The shield 43 is provided with four studs 46 and ends at the proximal end in a toothed ring 38.

This toothed ring 38 engages a second toothed ring 39 located on the locking element 44. The locking element 44 is further provided with a locking protrusion 49 located at the proximal end thereof.

The needle cannula 30 is in FIG. 13 mounted in the bottom surface 50, which bottom surface 50 is provided in the housing 40, preferably in the hub 41.

FIG. 13 shows the safety needle assembly with the shield 43 in the locked position, and FIG. 14 illustrates the inside surface of the housing 40 by showing the part of the housing 40 cut away in FIG. 13 seen from the backside.

The four studs 46 on the shield 43 is guided in first horizontal tracks 51 provided on the inside surface of the housing 40. The locking protrusion 49 on the locking element 44 abuts a planar surface 48 in its initiate position and is guided in a second horizontal track 52 as the shield 43 is moved in the proximal direction. Once the shield 43 has been moved all the way back to its most proximal position and the injection is executed, a not shown spring positioned between the bottom surface 50 and the locking element 44 will urge the locking element 44 and hence the shield 43 in the distal direction. During this movement, the angled fore front 47 of the locking protrusion 49 will engage a diagonal track 53 also provided in the inside surface of the housing 40. While the shield 43 moves back to its initiate position, the locking element 44 and hence the locking protrusion 49 will rotate approximately 180 degrees in the diagonal track 53 and engage a locking chamber 54 provided at the distal end of the diagonal track 53, which locking chamber 54 has a blocking surface 55 that a planar back front 56 of the locking protrusion 49 will abut rendering further movement of the shield 43 impossible. The first toothed ring 38 of the shield 43 and the second toothed ring 39 of the locking element 44 support this movement due to mutual engagement of the angled surfaces of the two rings 38, 39.

The shield 43 cannot be rotated relatively to the housing 40 due to the engagement of the studs 46 with the first horizontal tracks 51. Since rotation of the shield 43 is inhibited it is impossible to rotate the locking protrusion 49 of the locking element 44 backwards in the diagonal track 53, and the locking protrusion 49 will therefore remain in the locking chamber 54 thus rendering the safety needle assembly secured.

A window could be provided in the housing 40 through which window the locking chamber 54 can be viewed, such that the user can get a visible indication whether the safety needle assembly has been used or not.

Figure 16:
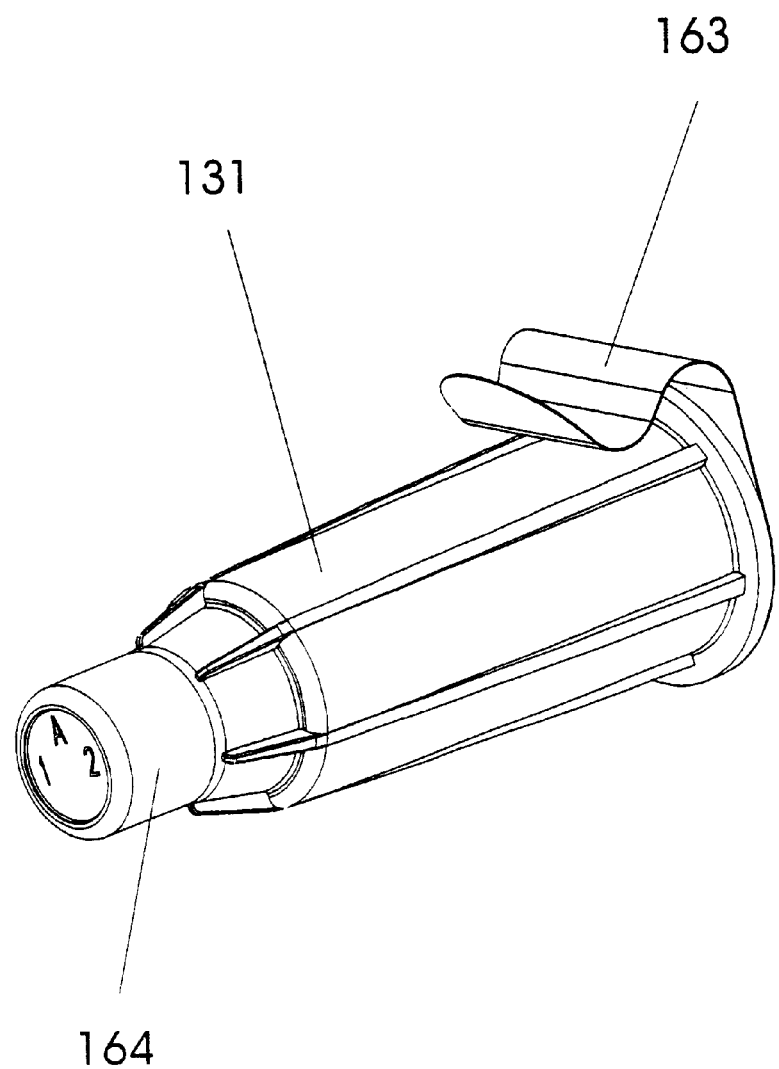
FIG. 16 Shows a perspective view of the safety needle assembly stored in a container.

An improved embodiment of the safety needle assembly disclosed in FIGS. 1 to 12 is shown in FIG. 15 and in FIG. 16.

In the following the numbers referring to the same element as in the previous figures has been given the same number plus one hundred.

The safety needle assembly shown in FIG. 15 comprises a housing made up from a needle hub 103 and a body 104 both preferably injection moulded from PP. Both the hub 103 itself and the tower of the hub 103 is somewhat higher than shown in FIG. 2, while the body 104 is somewhat shorter. The needle cannula 130 is inserted in the tower of the hub 103 and glued to the hub 103 by a blob of glue 160.

The body 104 is in this embodiment provided with three windows 120 and the locking element 116 is also provided with three locking protrusions 117. When the locking element 116 locks the safety needle assembly from reuse, the three locking protrusions 117 will be visible in the three windows 120 as earlier explained.

The shield 104 which is preferably made from TPX can be transparent such that the tip of needle cannula 130 is visible for inspection by the user prior to injection, has on its proximal end six studs 110. The toothed ring 113 formed between these studs 110 is therefore in this embodiment only provided with six valleys.

The locking element 116 which is preferably made from POM or PP is on the distal end surface provided with a serrated ring 161 which are used during the manufacturing process. When the safety needle assembly is being assembled a tool can enter the safety needle assembly through the needle outlet 107 in the shield 102 and engage this serrated ring 161 in order to rotate the locking element 116 to the correct position before the shield 102 and the locking element 116 is permanently encapsulated in the housing. For this purpose the needle outlet 107 needs to be large enough for the toll to pass through the needle outlet 107.

In the embodiment shown in FIG. 10 there exist a slight possibility of rotating the shield 2 when the studs 10 are longitudinal located between the fins 22 and the lower part 21b of the ribs 21. In order to prevent such accidental rotation, the studs 110 of the embodiment shown in FIG. 15 is provided with an additional guiding rib 162 which are guided in a number of not shown guiding tracks provided on the inside surface of the body 104 of the housing. Due to this no rotation between the shield 102 and the body 104 is possible, When the safety needle assembly is assembled the whole unit is packed in a container 131 which container 131 is sealed with a removable seal 163 and sterilized. The removable seal 163 is preferably made from paper.

The distal part of the container 131 can be formed as a cup 164 holding a predetermined volume as shown in FIG. 16. The dosage of an injection device to be used with the safety needle assembly can thus be controlled by ejecting a predetermined number of doses into the cup 164 and verifying the expelled volume. This can be done either by filling the entire cup or by having indications printed on the cup 164.

Some preferred embodiments have been shown in the foregoing, but it should be stressed that the invention is not limited to these, but may be embodied in other ways within the subject matter defined in the following claims.

List of Parts

1 Housing
2 Shield
3 Hub
4 Body
5 Connecting surface
6 Top surface
7 Needle outlet
8 Opening
9 Bottom surface
10 Stud
11 Planar ore front of studs
12 Angled back front of studs
13 Toothed ring
14 Planar surface
15 Blocking surface
16 Locking element
17 Locking protrusion
18 Angled front of locking protrusion
19 Planar back front of locking protrusion
20 Window
21 Rib
21a Upper part of rib
21b lower part of rib
22 Fin
23 Angled surface
24 Collar
25 Spring
26 Spaces on shield
27 Directional arrow
28 Directional arrow 29 Directional arrow
30 Needle cannula
31 Container
32 distal surface of container
33 proximal surface of container
34 Ribs on outside surface of housing
35 Thread
36 Front end of locking protrusion
37 Inner top end of shield
38 Toothed ring of shield
39 Second toothed ring of locking element
40 Housing
41 Hub
42 Body
43 Shield
44 Locking element
45 Opening
46 Studs
47 Angled fore front of locking protrusion
48 Planar surface
49 Locking protrusion
50 Bottom surface
51 First horizontal track
52 Second horizontal track
53 Diagonal track
54 Locking chamber
55 Blocking surface
56 Planar back front
102 Shield
103 Hub
104 Body
107 Needle outlet
110 Stud
113 Toothed ring
116 Locking element
117 Locking protrusion
120 Window
125 Spring
130 Needle cannula
131 Container
160 Glue
161 Serrated ring
162 Guiding rib
163 Seal
164 Cup

What is claimed is:

1. A Safety needle assembly comprising:
a cylindrical housing having a top surface and a bottom surface, said housing having means for mounting said housing onto a medical injection device,
a needle cannula mounted in the bottom surface, said needle cannula having a distal end located at a distal side of the bottom surface,
a shield telescopically movable relatively to the housing for movement between a distal position where the shield covers the distal end of the needle cannula and a proximal position where at least a part of the distal end of the needle cannula is exposed,
a spring located inside said housing urging the shield in the distal direction,
a locking element provided inside the housing and having at least one outwardly pointing locking protrusion
wherein
said locking element is a separate part provided between the spring and the shield and longitudinal moved simultaneously with the shield relatively to the housing during use, whereby the locking protrusion provided on the locking element is guided from a first position where the shield is in the distal position, via a second position where the shield is in the proximal position to a third position where the shield is in the distal position and in which third position at least one of the locking protrusions is blocked by a blocking surface provided on the inside surface of the housing whereby further movement of the shield is irreversible immobilized.

2. A safety needle assembly according to claim 1, wherein the locking protrusion of the locking element in the first position abuts a stud provided on the shield and a fin provided on the inside surface of the housing.

3. A safety needle assembly according to claim 2, wherein the locking element and the locking protrusion rotates relatively to the housing and the shield when an angled surface of the stud aligns an angled surface of the fin.

4. A safety needle assembly according to claim 3, wherein the locking protrusion of the locking element in the second position abuts a toothed ring provided at the proximal end of the shield.

5. A safety needle assembly according to claim 4, wherein the locking protrusion of the locking element in the third position is arrested in an opening in a longitudinal rib provided on the inside surface of the housing, which opening defines the blocking surface.

6. A safety needle assembly according to claim 5, wherein the guiding means for guiding the locking protrusion of the locking element comprises the ribs and the fins provided on the inside surface of the housing, which ribs and fins extends only in the horizontal direction.

7. A safety needle assembly according to anyone of the claim 1 wherein the shield is mounted inside the housing and penetrates through an opening at the top surface of the housing.

8. A safety needle assembly according to claim 7, wherein the spring interfaces the locking element and the bottom surface of the housing.

9. A safety needle assembly according to claim 8, wherein the housing is provided with a window through which window the locking protrusion is visible when the locking protrusion is in its third position.

* * * * *